United States Patent [19]

Calderazzo et al.

[11] Patent Number: 5,003,094

[45] Date of Patent: Mar. 26, 1991

[54] COMPLEX ANIONIC METAL SULFIDES AND PROCESS FOR THEIR PREPARATION

[75] Inventors: Fausto Calderazzo, Ghezzano; Daniela Belli Dell'Amico, Pisa, both of Italy

[73] Assignee: Consiglio Nazionale Delle Ricerche, Rome, Italy

[21] Appl. No.: 391,981

[22] Filed: Aug. 10, 1989

[30] Foreign Application Priority Data

Aug. 19, 1988 [IT] Italy ................. 21720 A/88

[51] Int. Cl.$^5$ ............... C07F 15/04; C07F 15/06; C07F 15/08; C07F 1/08
[52] U.S. Cl. ................................. 556/146; 556/113
[58] Field of Search ............... 556/138, 140, 146, 110, 556/113

[56] References Cited

U.S. PATENT DOCUMENTS

| | | | |
|---|---|---|---|
| 4,148,816 | 4/1979 | Rappas et al. | 556/146 |
| 4,279,829 | 7/1981 | Velenyi et al. | 556/146 X |

*Primary Examiner*—Arthur C. Prescott
*Attorney, Agent, or Firm*—Birch, Stewart, Kolasch & Birch

[57] ABSTRACT

Transition metal complex sulfides containing the $NH_2R_2{}^+$ group are prepared by treating the hydrogen sulfide an organic solution of a carbomate having the general formula:

$$Me^z(O_2CNR_2)_z$$

in which Me is a transition metal and R an alkyl group.

12 Claims, No Drawings

COMPLEX ANIONIC METAL SULFIDES AND PROCESS FOR THEIR PREPARATION

FIELD OF THE INVENTION

The present invention refers to complex metal sulfides employable as semi-conductors or as materials having photoelectric activity, and to a process for their preparation.

PRIOR ART

In recent years various investigations were made with the purpose of finding metal sulfides having photoelectric properties and processes for their preparation.

For example, the polycrystalline $FeS_2$ was prepared and characterized (A. Ennaoni, S. Fiechter et al "Photoactive synthetic polycrystalline pyrite" Electrochemical Science and Technology, 1579–82. July 1985).

A vast class of transition metal chalcogenides was also investigated (M. Tributsch, "Photoelectrochemical energy conversion involving transition metal d-states", Structure and Bonding 49, 127-175 1982).

More recently the use of alkoxides as intermediates for the formation of sulfides (H. P. Boehm, E. Flaig, Angew.Chem 78, 987, 1966) and of oxides (M. L. H. Chisholm, I. P. Rothwell, Alkoxides and Aryloxides, in G. Wilkinson, R. D. Gillard, J. A. McCleverty, Eds., Comprehensive Coordination Chemistry, Pergamon Press, Oxford, Vol. 2, 1987, pp. 335-364) has been thoroughly investigated.

SUMMARY OF THE INVENTION

We have found new complex anionic metal sulfides of general formula (i)

$$(NH_2R_2)_m Me^z_p S_q \quad (I)$$

in which m, q and p are bound by the following relationship:

$m = 2q - zp$ $R = C_2-C_5$ alkyl

Me = transition metal z = oxidation state

Said sulfides are prepared by dissolving in a anhydrous organic solvent a carbamate of general formula (II)

$$Me^z(O_2CNR_2)_z \quad (II)$$

followed by a treatment with hydrogen sulfide, filtration of the precipitate, washing with an organic solvent and drying.

DETAILED DESCRIPTION OF THE INVENTION

The characteristics and the advantages of the complex anionic metal sulfides of general formula (I) and of the process for their preparation will be further evidenced by the following detailed description.

The sulfides according to the present invention belong to transition metals, particularly, Fe, Co, Ni, Cu and other of series 3d, in their usual and less usual oxidation states.

The alkyl groups bound to the nitrogen atom, which may be equal or different, are the ones having 2 to 5 carbon atoms, in particular, ethyl, isopropyl, n- or iso-butyl, amyl.

For the preparation of the complex metal sulfides of general formula (I), the corresponding complex N,N-dialkylcarbamates of general formula (II) are dissolved in anhydrous organic solvents inert vis-a-vis the compounds in question.

Preferred solvents are aliphatic and aromatic hydrocarbons, particularly preferred are n-heptane and toluene. Mixtures of two or more hydrocarbons may also be employed.

The solution has a N,N-dialkylcarbamate concentration of between 1 and $10^{-2}$ moles/l. In certain cases one can avoid dissolving the prepared metal carbamate employing as starting materials the solutions obtained by treating the corresponding anhydrous metal halide with the secondary amine and $CO_2$, in a hydrocarbon solvent, after elimination of $NH_2 R_2X$ and by partially evaporating the excess amine used in the reaction for producing the carbamate.

The carbamate containing solution is treated with hydrogen sulfide at 0°-30° C. for 1 to 24 hrs.

The precipitate is filtered off, washed with a solvent of the type employed in the preparation and dried at room temperature under reduced pressure.

The yield is practically quantitative and the product shows high purity. It is sensitive to oxygen, and, in air, develops $SO_2$ and $H_2S$; by treatment with a concentrated hydrochloric acid solution in a inert atmosphere only $H_2S$ is evolved.

The obtained sulfides (I) show electrical characteristics suitable to their use as semiconductors and as materials having photoelectric activity.

The process according to the invention presents the following advantageous characteristics:

(a) as the dialkylcarbamate ($O_2CNR_2$) group contains the elements of carbon dioxides, it is an excellent exiting group.

(b) The presence of the $NR_2$ residual leads almost necessarily to the formation of anionic sulfides.

Finally, there is the possibility of exchanging the $NH_2R_2^+$ group with other cations, so as to obtain bimetallic sulfides.

As illustrative examples of the chemical reaction leading to the formation of the sulfides (I) according to the present invention, the following may be reported:

$6Co(O_2CNEt_2)_2 + 7H_2S \rightarrow (NH_2Et_2)_2Co_6S_7 + 12CO_2 + 10NHEt_2$ $8Ni(O_2CNEt_2)_2 + 9H_2S \rightarrow (NH_2Et_2)Ni_8S_9 + 16CO_2 + 14NHEt_2$ $8Fe(O_2CNEt_2)_3 + 15H_2S \rightarrow (NH_2Et_2)_6Fe_8S_{15} + 24CO_2 + 18NHEt_2$ $16Fe(O_2CNiPr_2)_3 + 29H_2S \rightarrow (NH_2iPr_2)_{10}Fe_{16}S_{29} + 48CO_2 + 38NHiPr_2$ The following examples of the preparation of sulfides (I) are reported to illustrate the present invention, without limiting it.

EXAMPLE 1

0.497 g ($1,71.10^{-3}$ moles) $Co(O_2CNEtPv2Pv)_2$ and 10 ml toluene. were introduced in a 100 ml distillation flask in a nitrogen atmosphere. After saturation with gaseous $H_2S$, the mixture was left under stirring at room temperature for one day. The black solid obtained was filtered off, washed with toluene and dried at room temperature with the aid of a mechanical pump ($10^{-2}$ torr) for 4 hrs. 0.152 g (73.4%) of a product was obtained which the analysis showed to correspond to $(NH_2Et_2)_2Co_6S_7$. Elemental analysis: found % (calculated for $C_8H_{24}N_2Co_6S_7$) C:11,6 (13,2); H:3,0 (3,3); N:3,0 (3,8); Co:48,6 (48,7), S:29,2 (30,9).

Resistivity = 490,88 $10^{-3}/\Omega$ cm

EXAMPLE 2

4.65 g (0.016 moles) $Ni(O_2CNEt_2)_2$ and 100 ml n-eptane were introduced in a 250 ml distillation flask in a nitrogen atmosphere.

After saturation with gaseous $H_2S$, the mixture was left under stirring at room temperature for 1 day. The black solid obtained was filtered off, washed with n-heptane and dried with the aid of a mechanical pump $10^{-2}$ torr) at room temperature for 10 hrs. 1.69 g (93%) of a solid were obtained which the analysis showed to correspond to $(NH_2Et_2)_2Ni_8S_9$.

Elemental analysis: found % (calculated for $C_8H_{24}N_2Ni_8S_9$) C:10.4 (10.6); H:2.6 (2.7); N:2.9 (3.1); Ni:50.5 (51.8); S:32.9 (31.8).

Resistivity = 350.624 $10^{-3}/\Omega$ cm

EXAMPLE 3

16.81 g (3.4 $10^{-2}$ moles) $[Fe(O_2CN\ iso\text{-}Pr_2)_3]_n$ and 160 ml of a 1/1 toluene-n-heptane mixture were introduced in a 200 ml distillation flask in a nitrogen atmosphere. After saturation with gaseous $H_2S$, the mixture was left under stirring at room temperature for one day. The black solid obtained was filtered off, washed with a 1/1 toluene-n-heptane mixture and dried at room temperature for 4 hrs with the aid of a mechanical pump ($10^{-2}$ torr). 5.22 g (85%) of a product corresponding at the analysis to the formula $(NH_2\ iso\text{-}Pr_2)_{10}Fe_{16}S_{29}$ wee obtained. Elemental analysis: % found (calculated for $C_{60}H_{160}Fe_{16}N_{10}S_{29}$):C,25.2(25.3);H,5.3);(5.7)-;Fe,31.7(31.4);N,4.2(4.9); S;31.5(32.7).

EXAMPLE 4

9.66 g (2.39 $10^{-2}$ moles) of $[Fe(O_2CNEt_2)_3]_n$ and 100 ml toluene were introduced in a 250 ml distillation flask in a nitrogen atmosphere. After saturation with gaseous $H_2S$, the mixture was left under stirring at room temperature for 1 day. The black solid obtained was filtered off, washed with toluene and dried with the aid of a mechanical group ($10^{-2}$ torr) at room temperature for 4 hrs. 3.98 g (97%) of a product corresponding by analysis to $(NH_2Et_2)_6Fe_8S_{15}$ were obtained.

Elemental analysis: % found (calculated for $C_{24}H_{72}Fe_8N_6S_{15}$); C,21.0(21.0); H, 5.2(5.3); Fe, 30.4(32.5); N,6.0(6.1); S, 35.8(35.0).

Resistivity = 157.08 $10^4\ \Omega$ cm

EXAMPLE 5

Anhydrous cupric chloride (3.79 g, 29.2 mole) prepared from the hydrated form by treatment with thionyl chloride, was suspended in anhydrous toluene (100 ml) in a nitrogen atmosphere. After evacuating the system, carbon dioxide at normal pressure and 19.88 g diethylamine (272 moles) were added and the mixture was stirred for 5 hrs at room temperature.

The colorless precipitate consisting of diethylammonium chloridrate was filtered off and the blue colored solution was concentrated under reduced pressure and at room temperature to about half of its initial volume.

The resulting solution, containing copper (II) N,N-diethylcarbamate, $Cu(O_2CNEt_2)_2$, was treated with $H_2S$ previously dried through calcium chloride absorption tower. Immediate precipitation of a black solid was observed. The $H_2S$ treatment was repeated several times to make sure that the reaction was completed. The complex cupric sulfide obtained was filtered off, repeatedly washed with toluene and dried with for 14 hrs at room temperature with the aid of a mechanical pump (2.09 g; 66% yield on the basis of the copper content of this product). The results of the analysis correspond to a composition $[NH_2(C_2H_5)_2]_2[Cu_{14}S_{15}]$.

Elemental analysis: found % (calculated for $C_8H_{24}Cu_{14}N_2S_{15}$); C, 6.0(6.3); H, (1.6); Cu, 56.3(58.6); N, 1.6(1.8).

Resistivity = 147,26 $10^{-3}\Omega$ cm.

EXAMPLE 6

Example 5 was repeated for preparing a solution of copper (II) N,N-di-isopropylcarbamate, $Cu\ (O_2C\text{-}NiPr_2)_2$, which was then treated with $H_2S$ as in Example 5, to obtain the corresponding isopropyl cupric sulfide.

Resistivity = 490.88 $10^{-3}/\Omega$ cm.

We claim:

1. Complex anionic metal sulfides having the general formula (I):

$$(NH_2R_2)_mMe^z_pS_q \qquad (I)$$

ion which m, q and p are bound by the following relation:

$m = 2q - zp$
$R = C_2\text{-}C_5$ alkyl
Me = transition metal
z = oxidation state 2. Sulfides according to claim 1, wherein said transition metal may be Fe, Co, Ni, Cu or another metal of the 3d series in their usual and less usual oxidation states.

3. Sulfides according to claim 1, wherein said alkyl is: ethyl, isopropyl, butyl, amyl.

4. Process for the preparation of complex anionic metal sulfides of general formula (I)

$$(NH_2R_2)_mMe^z_pS_q \qquad (I)$$

in which m, p and q are bound by the following relation:
$m = 2q - zp$
$R = C_2\text{-}C_5$ alkyl
Me = transition metal
z = oxidation state wherein a solution containing the corresponding carbamates of general formula (II)

$$Me^z(O_2CNR_2)_z \qquad (II)$$

in inert, anhydrous organic solvents, is treated with hydrogen sulfide and the precipitate in filtered off, washed and dried.

5. Process according to claim 4, wherein the solution, treated with hydrogen sulfide, is the solution obtained by treating the anhydrous metal halide with a secondary amine and $CO_2$ in a hydrocarbon solvent, after the $NH_2R_2X$ has been eliminated from said solution, and after partial evaporation to eliminate the excess of the amine employed in the reaction for obtaining the carbamate.

6. Process according to claim 4, wherein said organic solvents are aliphatic and aromatic hydrocarbons.

7. Process according to claim 4, wherein said solvents are n-heptane, toluene or their mixtures.

8. Process according to claim 4, wherein the organic solvent solution has a concentration of said carbamate of between 1 and $10^{-2}$ moles/l.

9. Process according to claim 4, wherein said hydrogen sulfide treatment is performed at a temperature between 0° and 30° C.

10. Process according to claim 4, wherein said hydrogen sulfide treatment is continued for 1 to 24 hours.

11. Process according to claim 4, wherein said drying of the product is performed under reduced pressure at room temperature.

12. Complex anionic metal sulfides having the formula $$(NH_2R_2)_m Ni^z_p S_q$$

in which m, q, and p are bound by the following relation:
m = 2q − zp,
R = $C_2$-$C_5$ alkyl, and
z = oxidation state.

* * * * *